United States Patent [19]

Rickloff et al.

[11] Patent Number: 5,508,009

[45] Date of Patent: *Apr. 16, 1996

[54] OPTIMUM HYDROGEN PEROXIDE VAPOR STERILIZATION SYSTEM

[75] Inventors: James R. Rickloff, Cary; Donald C. Upchurch, Apex; Robert W. Childers, Garner, all of N.C.

[73] Assignee: American Sterilizer Company, Erie, Pa.

[ * ] Notice: The term of this patent shall not extend beyond the expiration date of Pat. No. 5,445,792.

[21] Appl. No.: 442,468

[22] Filed: May 16, 1995

Related U.S. Application Data

[62] Division of Ser. No. 237,406, May 2, 1994, Pat. No. 5,445,792, which is a continuation of Ser. No. 851,179, Mar. 13, 1992, abandoned.

[51] Int. Cl.$^6$ ........................................................ A61L 2/00
[52] U.S. Cl. ........................... 422/292; 422/105; 422/108; 422/110; 422/295; 422/297; 422/300; 422/306
[58] Field of Search ................................. 422/1, 28, 32, 422/33, 34, 292, 295, 297, 300, 306, 905, 105, 108, 110

[56] References Cited

U.S. PATENT DOCUMENTS

| | | | |
|---|---|---|---|
| Re. 33,007 | 8/1989 | Bier | 203/12 |
| 3,948,601 | 4/1976 | Fraser et al. | |
| 4,064,886 | 12/1977 | Heckele | 134/95 |
| 4,164,538 | 8/1979 | Young et al. | |
| 4,169,123 | 9/1979 | Moore et al. | 422/29 |

(List continued on next page.)

FOREIGN PATENT DOCUMENTS

| | | |
|---|---|---|
| 0302402A2 | 8/1989 | European Pat. Off. |
| 3334999A | 4/1985 | Germany . |
| 3334999C | 10/1986 | Germany . |
| 4102055A1 | 9/1990 | Germany . |
| 2-10505 | 1/1990 | Japan . |
| 3-68331 | 3/1991 | Japan . |
| 3-94759 | 4/1991 | Japan . |
| 3-82436 | 4/1991 | Japan . |
| 3-111026 | 5/1991 | Japan . |
| 3-106332 | 5/1991 | Japan . |
| 3-123531 | 5/1991 | Japan . |
| 3-151931 | 6/1991 | Japan . |
| 3-176022 | 7/1991 | Japan . |
| 3-176061 | 7/1991 | Japan . |
| 3-221027 | 9/1991 | Japan . |
| 3-295535 | 12/1991 | Japan . |
| 463240B | 10/1990 | Sweden . |
| 1519701A | 11/1989 | U.S.S.R. . |
| 1582060 | 12/1980 | United Kingdom . |
| 2052800A | 1/1981 | United Kingdom . |
| 2105591A | 3/1983 | United Kingdom . |
| 2127692A | 4/1984 | United Kingdom . |
| 2105591 | 4/1985 | United Kingdom . |
| 2191585A | 12/1987 | United Kingdom . |

OTHER PUBLICATIONS

Steris System 1™ Processor–Operator Manual, 1988, by Steris Corporation.
Instrumental in Your Practice (description of STATIM cassette, date unknown, but prior to Apr. 23, 1991.
VHP™ Technology a Collection of Scientific Papers, First Edition Jan. 1, 1992, published by AMSCO Scientific.

Primary Examiner—Robert J. Warden
Assistant Examiner—Krisanne M. Thornton
Attorney, Agent, or Firm—Jones, Day, Reavis & Pogue

[57] ABSTRACT

A sterilization method is provided which includes the steps of measuring the pressure within a sterilization chamber injecting a sterilant vapor into a flow of carrier gas, introducing the sterilant vapor and carrier gas into and through a sterilization chamber, and adjusting the rate of sterilant vapor injection to reach a pre-determined percentage of saturation limit for the sterilant vapor in the chamber, immediately following the introduction of sterilant vapor and carrier gas into the chamber, in response to the measured pressure. The predetermined saturation limit is selected to optimize the rate of sterilization, while avoiding substantial condensation of the sterilant.

4 Claims, 5 Drawing Sheets

U.S. PATENT DOCUMENTS

| | | | |
|---|---|---|---|
| 4,169,124 | 9/1979 | Forstrom et al. | 422/33 |
| 4,230,663 | 10/1980 | Forstrom et al. | 422/33 |
| 4,261,950 | 4/1981 | Bainbridge et al. | 422/26 |
| 4,278,101 | 7/1981 | Tanaka et al. | 134/167 C |
| 4,281,674 | 8/1981 | Tanaka et al. | 134/95 |
| 4,282,179 | 8/1981 | Gunther . | |
| 4,299,244 | 11/1981 | Hirai | 134/102 |
| 4,337,223 | 6/1982 | Kaye . | |
| 4,380,530 | 4/1983 | Kaye | 422/300 |
| 4,410,492 | 4/1983 | Kaye | 422/27 |
| 4,449,518 | 5/1984 | Konomura et al. | 128/4 |
| 4,489,741 | 12/1984 | Ogasawara | 134/179 |
| 4,525,220 | 6/1985 | Sasa et al. | 134/21 |
| 4,526,622 | 7/1985 | Takamura et al. | 134/21 |
| 4,526,623 | 7/1985 | Ishii et al. | 134/21 |
| 4,537,209 | 8/1985 | Sasa | 134/166 C |
| 4,579,597 | 4/1986 | Sasa et al. | 134/21 |
| 4,579,598 | 4/1986 | Sasa . | |
| 4,642,165 | 2/1987 | Bier | 203/12 |
| 4,648,978 | 3/1987 | Makinen et al. | 210/759 |
| 4,687,635 | 8/1987 | Kaehler et al. | 422/26 |
| 4,730,729 | 3/1988 | Monch . | |
| 4,731,222 | 3/1988 | Kravolic et al. | 422/37 |
| 4,732,187 | 3/1988 | Monch | 134/135 |
| 4,744,951 | 5/1988 | Cummings et al. | 422/28 |
| 4,748,007 | 5/1988 | Gaudion et al. | 422/300 |
| 4,763,678 | 8/1988 | Ott | 134/174 |
| 4,843,867 | 7/1989 | Cummings | 73/23 |
| 4,844,052 | 7/1989 | Iwakoshi et al. . | |
| 4,862,872 | 7/1989 | Yabe et al. | 128/6 |
| 4,863,688 | 9/1989 | Schmidt et al. | 422/28 |
| 4,892,706 | 1/1990 | Kravolic et al. | 422/28 |
| 4,909,999 | 3/1990 | Cummings et al. | 422/298 |
| 4,935,371 | 6/1990 | Rickloff | 435/296 |
| 4,941,519 | 7/1990 | Sestak et al. | 141/22 |
| 4,943,414 | 7/1990 | Jacobs et al. | 422/28 |
| 4,952,370 | 8/1990 | Cummings et al. | 422/28 |
| 4,956,145 | 9/1990 | Cummings | 422/28 |
| 4,965,145 | 9/1990 | Cummings et al. | 422/28 |
| 4,973,449 | 11/1990 | Kolstad et al. . | |
| 5,068,087 | 11/1991 | Childers | 422/26 |

OPTIMUM HYDROGEN PEROXIDE VAPOR STERILIZATION SYSTEM

This is a divisional of application Ser. No. 08/237,406 filed on May 2, 1994 now U.S. Pat. No. 5,445,792, which is a continuation of 07/851,179 filed Mar. 13, 1992 (now abandoned).

FIELD OF THE INVENTION

The present invention relates generally to sterilization methods, and more particularly to a method of vapor phase sterilization utilizing hydrogen peroxide.

BACKGROUND OF THE INVENTION

It is generally desired to sterilize medical instruments, such as endoscopes having long, narrow lumens, and dental tools, before use. In medical facilities, where instruments need to be used several times per day on different patients, it is important not only to sterilize the instruments between patients to prevent cross-contamination, but to do so quickly and economically without damaging the instruments.

Several different methods have been developed for delivering sterilant vapor to a chamber for sterilizing medical instruments or other loads. In one option, the "deep vacuum" approach, a deep vacuum is used to pull liquid sterilant into a heated vaporizer; once vaporized, the sterilant is propelled by its vapor pressure into the evacuated chamber. In another option, the "flow-through" approach, vaporized sterilant is mixed with a carrier gas and delivered to the sterilization chamber under slightly negative or position pressure.

In yet a different approach, the sterilant vapor is introduced into the chamber under a combination of deep vacuum and flow-through conditions, in one cycle, to obtain a more efficacious sterilization than is achieved by the prior flow-through process or static, deep vacuum process alone. The combination vacuum/flow-through sterilization method is disclosed in commonly assigned, copending application U.S. Ser. No. 07/851,415, entitled "Sterilization Method for Multicomponent Sterilant," now abandoned in favor of copending continuation application Ser. No. 08/279,688, filed on Jul. 25, 1994 and incorporated by reference herein. In one embodiment described therein, a deep vacuum is first drawn in the sterilization chamber, followed by the injection of pulses of the sterilant vapor until a higher, second subatmospheric chamber pressure is reached. After sterilant vapor has been allowed to permeate the chamber and its contents, sterilant vapor is injected in pulses and flowed with a carrier gas into, through, and out of the chamber, during a transition phase, in which the chamber pressure reaches a higher third subatmospheric pressure, and then a fourth subatmospheric pressure, which is equal to a higher than the third subatmospheric pressure. The cycle then enters a flow-through phase at the fourth subatmospheric pressure, which includes successive alternating periods of sterilant and carrier gas flow and discontinuance of such flow. Sterilant vapor and carrier gas are preferably injected in successive pulses during the transition and flow-through phases, to increase sterilant penetration. At the end of the flow-through phase, there are one or more aeration steps to remove sterilant from the chamber.

When the above-described vacuum/flow-through method is used to sterilize a lumened instrument having at least two open ends and a fluid flow path between the open ends, one end of the instrument may be fluidly coupled to either the exhaust port or inlet port of the chamber. Sterilant vapor is thereby flowed through the lumens and also bathes the external surfaces of the instrument, when sterilant vapor is carried into and exhausted from the chamber.

If various types of lumened instruments, in particular, long and narrow endoscopes, are sequentially placed in and coupled to the sterilization chamber, and subjected to the same combination vacuum/flow-through sterilization cycle, the different orifice sizes, lengths, and shapes of the instruments may present varying degrees of restriction to the flow of carrier gas and sterilant vapor. The different instruments may thereby produce different final pressure levels and rates of chamber pressure increases as the sterilization cycle progresses from deep vacuum to flow-through conditions. The actual chamber pressure levels reached during the cycle phases will also depend on the day-to-day atmospheric pressure conditions.

It is desired to effectively and automatically control the amount of sterilant vapor delivered to a sterilization chamber, during the varying chamber pressure conditions which may be experienced during a sterilization cycle, or from cycle to cycle, to maximize sterilant vapor exposure. The level of sterilant vapor, however, should not exceed its saturation limit under the sterilization conditions. Otherwise, sterilant will condense, decreasing the amount of sterilant vapor available for sterilization. Also, condensed sterilant, such as hydrogen peroxide may degrade or harm the contents of the sterilization chamber. Synthetic materials, such as are employed in flexible endoscopes, for example, may be damaged by condensed hydrogen peroxide.

There is a need for a sterilization method which automatically provides optimum sterilant vapor exposure under varying pressure conditions which may occur within a vacuum combination flow-through cycle, for example, and/ or from cycle-to-cycle, with different instrument loads and different atmospheric pressures. There is also a need for a sterilization method which avoids condensation resulting from exceeding the saturation limit of the sterilant vapor. There is a further need for an efficient sterilization method that can be economically implemented, with increased instrument through-put.

SUMMARY OF THE INVENTION

The present invention provides an optimum method of vapor sterilization. The method succeeds in automatically controlling the sterilant vapor content within a sterilization chamber at a predetermined percentage of the instantaneous saturation limit during those portions of a sterilization cycle in which the sterilant vapor is delivered into the sterilization chamber with a carrier gas. The saturation limit percentage is selected to ensure effective and efficient sterilization, without substantial condensation.

It has been discovered that the percentage of sterilant vapor saturation limit employed during the sterilization cycle, in addition to and separately from the concentration of hydrogen peroxide vapor, determines the rate of sterilization or efficacy of sterilization over a given period of time. By automatically adjusting the rate of sterilant vapor injected into the carrier gas, in response to varying chamber pressure conditions, the saturation limit percentage can be maximized throughout the sterilization cycle, thereby optimizing sterilization kill times. At the same time, the sterilization limit percentage can be maintained sufficiently below the level at which substantial condensation occurs, thereby ensuring effective sterilization and minimizing material compatibility problems resulting from contact of the condensed sterilant with the instrument load.

In accordance with the present invention, sterilant vapor is injected into a flow of carrier gas, and the mixture of sterilant vapor and carrier gas is introduced into the sterilization chamber during at least a portion of the sterilization cycle. Prior to injecting the sterilant vapor into the carrier gas, the pressure in the sterilization chamber is measured. The rate of sterilant vapor injection is adjusted to reach a predetermined percentage of the instantaneous saturation limit for the sterilant vapor, immediately following introduction of the sterilant vapor and carrier gas into the chamber, in response to the measured pressure.

In a particularly economical embodiment of the invention, the rate of sterilant vapor injection is automatically adjusted in response to range of pressures, which includes the measured pressure prior to injection, to reach a predetermined range of saturation limit percentages.

The saturation limit percentage is preferably maintained at above about 70% and below about 100%. More preferably, the saturation limit is maintained between about 85% and about 95%.

BRIEF DESCRIPTION OF THE DRAWINGS

The present invention can be better understood by reference to the drawings in which.

DETAILED DESCRIPTION OF THE INVENTION

Figure 1:
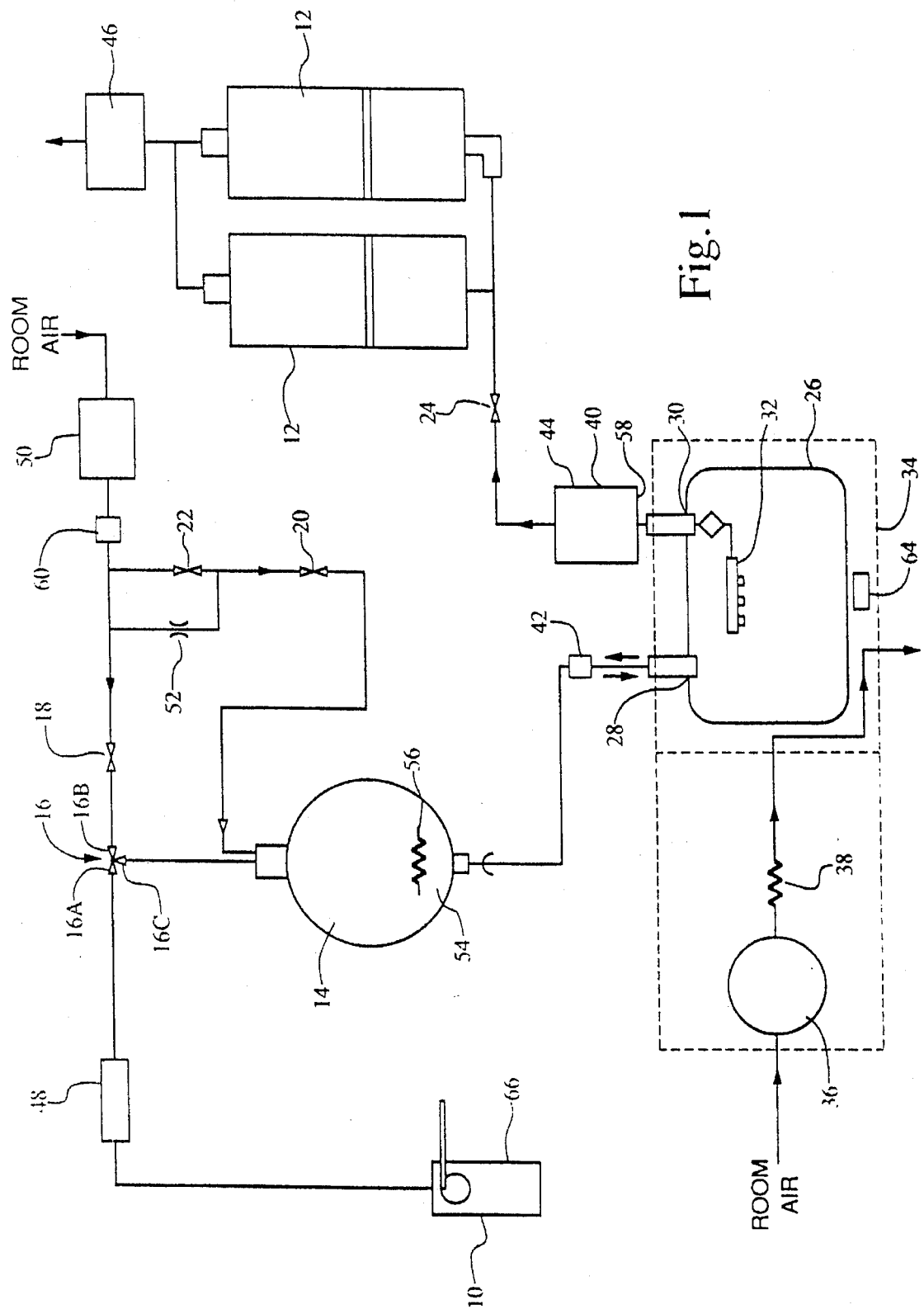
FIG. 1 is a schematic diagram of an exemplary sterilizer system in which the method of the present invention can be practiced.

The present invention may be used to optimize the efficacy of sterilization achieved over a given period of time and/or to shorten the time required to sterilize a variety of instruments, or items which may be present or loaded into the sterilization chamber or other sealed enclosure, such as surgical or dental tools. The invention is particularly suited for sterilizing endoscopes or other instruments having long, narrow lumens, which may provide varying degrees of flow resistance. The invention may also be used to sterilize the interior of a sterilization chamber, or other sealed enclosure, with or without a load.

The invention may be practiced with hydrogen peroxide as the vapor sterilant, using air (including room air) as the carrier gas. Preferably, the hydrogen peroxide vapor is generated from 30–35 percent (by weight) aqueous hydrogen peroxide solution. It is contemplated that other condensible gas sterilants and other inert gas carriers, such as nitrogen, may be used in the method of the invention.

The invention can be practiced with any sterilization system or sterilization cycle, where the sterilization system allows sterilant vapor to be carried into, through, and out of the sterilization chamber from the vaporizer, with a flow of carrier gas, during a portion of the cycle. The invention is particularly useful where varying chamber pressures may be experienced during a cycle or from cycle-to-cycle. For example, the invention is particularly suited for use with a combination deep vacuum/flow-through cycle, in which the chamber pressure increases as the cycle progresses from deep vacuum to flow-through conditions, through a transition phase. The rate of pressure increase, and the actual pressure levels obtained may vary during such a cycle or from such cycle-to-cycle, depending, for instance, on the nature of the instrument load (i.e., the degree of flow restriction presented by the load), and the level of atmospheric pressure.

The method of the invention succeeds in maximizing the percentage of saturation limit achieved for the sterilant vapor in the sterilization chamber, in response to chamber pressure. By maintaining the concentration of sterilant to a high percentage of its saturation limit, in response to chamber pressure, cycle time can be reduced and/or greater assurance of sterilization realized.

In the method of the present invention, there is no need to wait until a pre-determined pressure level is reached, before injecting sterilant at a constant rate into the system, to ensure that a pre-determined percentage of saturation limit is maintained. Instead, the sterilant can be immediately injected, at a rate adjusted to provide the pre-determined saturation limit percentage, in the sterilization chamber immediately after introduction of the sterilant vapor and carrier gas, at the chamber pressure measured prior to injection. Thus, the throughput of the sterilization system is increased, and/or greater assurance of effective sterilization over a given period is provided.

In accordance with the invention, the rate of sterilant vapor injected into the flow of carrier gas is automatically adjusted in response to chamber pressure, to maintain a pre-determined maximum percentage of the saturation limit for the sterilant, during at least a portion of the cycle in which sterilant vapor is flowed through the sterilization chamber with carrier gas. The percentage of saturation limit is preferably maintained at above about 70% and below about 100%, and more preferably between about 85% and about 95%. The rate of injection must be, at most, just below the amount than would saturate the mixture and cause substantial condensation.

The manner in which the method of the present invention is practiced, will now be described with reference to FIG. 2, which illustrates an exemplary combination vacuum/flow-through cycle. The illustrated cycle is particularly designed for sterilizing a flexible endoscope using hydrogen peroxide vapor generated from about 30% to about 35% (by weight) hydrogen peroxide solution, with room air as the carrier gas. As stated previously, it is contemplated that other sterilization cycles may be used to practice the present invention.

Figure 2:
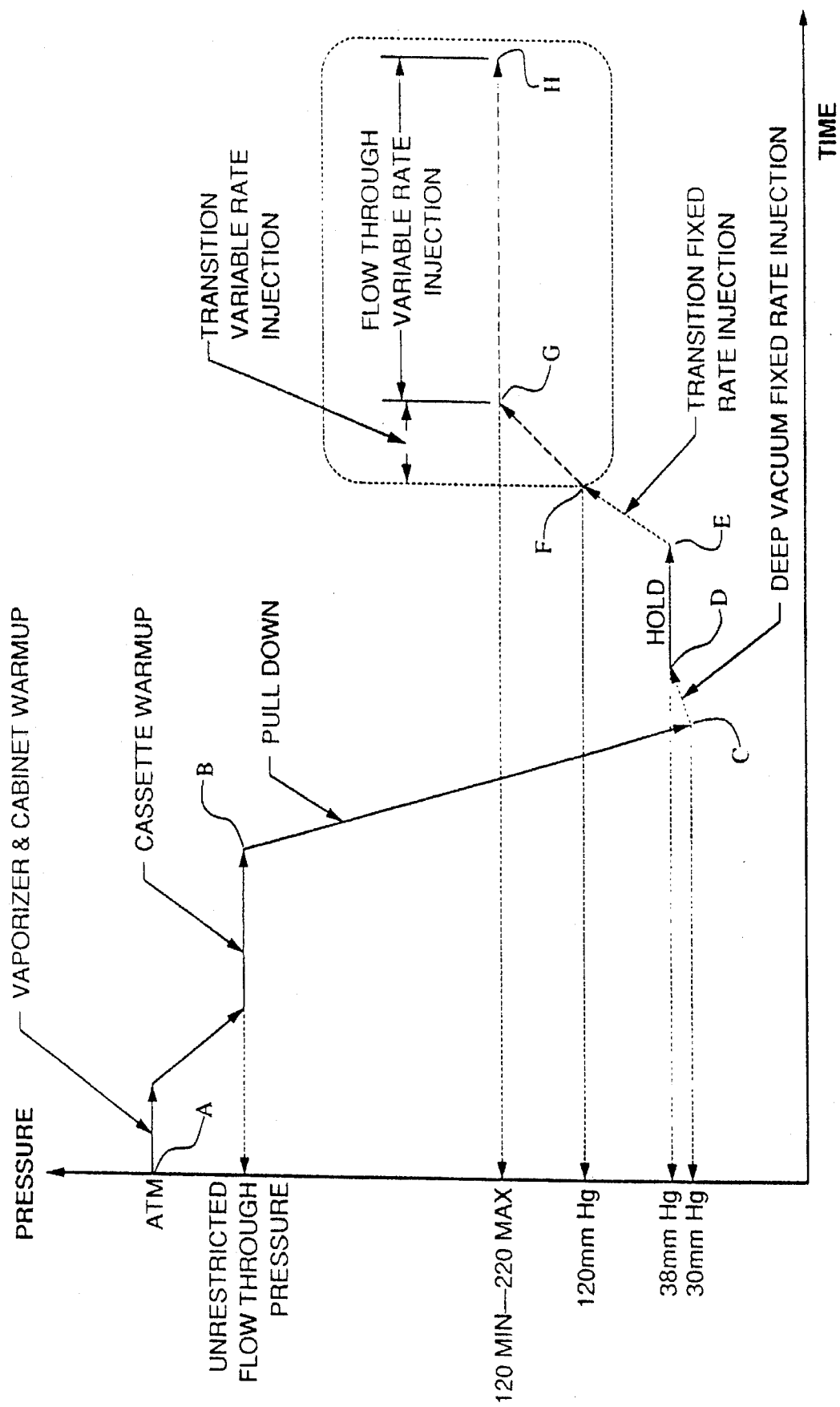
FIG. 2 is a graph of an exemplary endoscope sterilization cycle for which the method of the present invention can be practiced.

As indicated in FIG. 2, the representative sterilization cycle is preceded by a warming phase (points A to B), in which the temperature of the sterilization chamber and its contents increases from ambient temperature up to about 40° C., and preferably about 38° C. (100° F.), while the vaporizer temperature increases from ambient to about 120° C. (250° F.). Then, the sterilization cycle generally proceeds from a deep vacuum phase (points B to E), a transition phase (points E to G), and a flow-through phase (points G to H).

At the end of the flow-through phase, the system is aerated to remove sterilant from the chamber.

At pre-determined times in each phase of the sterilization cycle, aqueous hydrogen peroxide solution is delivered to the vaporizer in nearly continuous pulses or increments. The amount of sterilant delivered over a given period of time is controlled by the pulsing on/off time of the a suitable high-speed actuation, repeatable injection valve, preferably having a liquid supply orifice which is sufficiently small to overcome variations in delivery that may be caused by the length of the supply line (the distance between the valve and the vaporizer), and the vacuum pressure level.

In the vaporizer, each increment is substantially vaporized and drawn in vapor form, into the chamber. Vaporized sterilant is carried from the vaporizer to the sterilization chamber by a negative pressure differential (created by evacuating the sterilization chamber) and/or by a nearly continuous, pulsing air flow (the vaporized sterilant is, in effect, injected into the flow of carrier gas in the vaporizer).

The successive increments of liquid (and air) are delivered so that there is almost a steady stream of such increments to the vaporizer and almost a steady stream of vapor (and air) to the sterilization chamber. The incremental vaporization effectively overcomes the preferential vaporization of water over hydrogen peroxide and permits the vapor to maintain substantially the same relative concentrations of water and hydrogen peroxide as its liquid source. The overall method of incremental vaporization is described in U.S. Pat. No. RE 33007; reissued from U.S. Pat. No. 4,642,165, incorporated by reference herein.

In the exemplary cycle represented by FIG. 2, the rate of sterilant delivery to the vaporizer (which corresponds to the rate of sterilant injection into the air flow) is adjusted, pursuant to the present invention, in response to the chamber pressure measured prior to injection, during the portion of the transition phase where the pressure is less rapidly increasing (points F to G) and the flow-through phase (points G to H). These portions of the cycle are enlarged in FIG. 3.

In the deep vacuum phase, the sterilization chamber is evacuated (pulled down) to an absolute pressure less than or equal to about 30 mm Hg (points B to C). Aqueous hydrogen peroxide is then injected, in nearly continuous pulses at a fixed delivery rate into the vaporizer (points C to D). The vapor pressure of the sterilant carries it (due to the presence of the vacuum) in nearly continuous pulses to the sterilization chamber, causing the chamber pressure to rise about 8–13 mm Hg. Room air is preferably also pulsed into the vaporizer, during this part of the cycle, to provide a slight positive pressure, which assists in conveying sterilant vapor to the chamber. A brief holding period (points D to E) concludes the deep vacuum phase.

During the first portion of the transition phase (points E to F), hydrogen peroxide solution is injected at a fixed delivery rate (which, while not optimum, is acceptable for the short transition time) in nearly continuous pulses, into the vaporizer, where the vaporized hydrogen peroxide is carried by a nearly continuous pulsing flow of room air to the sterilization chamber. The chamber pressure rapidly increases to about 120 mm Hg.

During the second portion of the transition phase (points F to G), the nearly continuous pulses of hydrogen peroxide and air continue, and the chamber pressure rises to between about 120 mm Hg and about 220 mm Hg. The nearly continuous pulses of hydrogen peroxide and air into the chamber continue through the flow-through phase (points G to H), at a pressure between about 120 mm Hg and about 220 mm Hg. In the second portion of the transition phase and the flow through phase, hydrogen peroxide solution is injected at a variable rate, adjusted in response to the chamber pressure measured prior to injection, pursuant to the method of the present invention.

In order to determine the rate of sterilant delivery required to achieve the instantaneous, pre-determined percentage of saturation limit, at the chamber pressure measured prior to injection, a series of complex and interactive calculations must be made.

First, it needs to be recognized that air flowing through an evaluated sterilization system expands in volume, thereby diluting the humidity of the air carrier stream, and permitting a higher saturation concentration of sterilant vapor. Thus, as the pressure in the system increases, progressing through the transition and flow-through phases, the humidity also increases, decreasing the saturation concentration limit of sterilant vapor. In accordance with the present invention the rate of sterilant delivery is decreased when chamber pressure increases, to maintain a pre-determined percentage of the saturation limit.

The relationship between chamber pressure and humidity may be explained by reference to the Ideal Gas Law, and the law of partial pressures (which states that the total pressure of a mixture of gases equals the sum of the individual or partial pressures). If each gas's pressure is decreased or increased uniformly, as the sterilization cycle progresses, then an Ideal Gas Law ratio for a first and second chamber pressure, yields the following:

$$\frac{P_1 V_1}{P_2 V_2} = \frac{N_1 R T_1}{N_2 R T_2}$$

Where
P=Partial Water Vapor Pressure
V=$V_1$=$V_2$=Chamber Volume
R=Ideal gas constant
T=Chamber Temperature
N=Moles of Water Vapor Present Assuming T=$T_1$=$T_2$, a rearrangement of the foregoing equation combined with the assumption of uniform increase or decrease in partial pressure yields:

$$\frac{N_1/V}{N_2/V} = \frac{P_1}{P_2} = \frac{P \text{ chamber}_1}{P \text{ chamber}_2}$$

The ratio of N/V for water vapor is essentially a measure of humidity. Thus:

$$\frac{\text{Humidity}_1}{\text{Humidity}_2} = \frac{P \text{ chamber}_1}{P \text{ chamber}_2}$$

Thus, for example, operation at ½ atmosphere is equivalent to operation at 1 atmosphere, but at half the humidity level.

By first measuring the atmospheric pressure and humidity of room air, before the sterilization cycle begins, and assuming that these parameters and the ambient temperature remain constant, the relative humidity in the chamber at any point during the sterilization cycle, can be determined, based on the chamber pressure sensed at that point:

$$RH \text{ chamber} = RH \text{ ambient} \times \frac{P \text{ chamber}}{P \text{ atm}}$$

By combining the calculated relative humidity in the chamber, with the chamber temperature, the instantaneous saturation limit of the vapor mixture (C sat), immediately following introduction of sterilant vapor and carrier gas into the chamber can be calculated, as described in U.S. Pat. No. 4,956,145, incorporated by reference herein. (Although, as described therein, this calculation may be based on known data, it would not be immediately apparent to use such data, for the purposes of the present invention, because such data describes natural conditions wherein the vapors are in equilibrium with corresponding mixtures. The vapor mixture of the present invention, as previously stated, is preferably one that is flashed vaporized to produce higher concentrations of hydrogen peroxide than would be found with natural vaporization from a solution.)

The rate at which sterilant can be injected into the vaporizer and air flow, to reach the pre-determined percentage of the instantaneous saturation limit, can now be calculated from (and by subsequent rearrangement of) the following equation:

$$C\ sat \times \%\ sat = \frac{IR \times W}{AF\ \text{chamber}}, \text{where:}$$

C sat = the saturation limit for the sterilant vapor, in mg/l;

% sat = the predetermined percentage of saturation limit to be maintained;

IR = the injection rate of hydrogen peroxide vapor into the air stream (which corresponds to the injection rate of aqueous hydrogen peroxide solution into the vaporizer), in mg/min;

W = the weight percentage of hydrogen peroxide in the hydrogen peroxide/water vapor; and AF chamber = the air flow through the chamber, in L/min.

The air flow through the chamber may be calculated from the air flow at the pump outlet, based on application of Ideal Gas Law principles, to account for varying pressure and temperature conditions in the sterilization chamber, as follows:

$$AF\ \text{chamber} = AF\ \text{pump} \times \frac{P\ \text{atm} \times T(°K.)\ \text{chamber}}{P\ \text{chamber} \times T(°K.)\ \text{ambient}}$$

In the above equation, AF pump equals the air flow at the pump outlet, in L/min, and may be measured by a flow meter, or determined from data supplied by the pump manufacturer, in a manner known to those of ordinary skill in the art.

In general, the ambient temperature and chamber temperature (or temperature of sterilization) will remain constant (unlike the chamber pressure), during the sterilization cycles used in practicing the present invention. Thus, the temperature correction in the above calculation will generally be a constant. However, it is also contemplated than these temperatures may be allowed to vary during the sterilization cycle, in the method of the present invention. By measuring these temperatures prior to injection, and accounting for the varying chamber and ambient temperatures in the foregoing calculation, the rate of sterilant injection can also be regulated, to maintain a predetermined saturation limit percentage, in response to varying temperatures.

Similarly, it is also contemplated that the ambient relative humidity may vary during the practice of the method of the present invention. By measuring the ambient relative humidity of air flowed through the system, and entering the measured relative humidity into the above-described calculations, the rate of sterilant injection can also be regulated to maintain a predetermined saturation limit percentage, in response to varying ambient relative humidities.

While the method may be accomplished via manual operations, it is preferably controlled by a suitable microprocessor. The microprocessor receives an input signal from a pressure sensor, which is representative of the chamber pressure, and optionally an input signal from a temperature sensor, which is representative of the chamber temperature. In addition no these input signals, the microprocessor may receive additional data utilized in the above-described calculations for determining sterilant injection rate, such as ambient pressure, ambient temperature, ambient relative humidity, the weight percent of hydrogen peroxide in the vapor phase, and air flow rates. Such additional input data can be received by additional sensors (such as a humidity sensor), where appropriate, or input by an operator through a keypad. The microprocessor also preferably receives an input signal from a second temperature sensor, which is representative of vaporizer temperature, and a clock to monitor the progress of the sterilization cycle.

The saturation limits for hydrogen peroxide vapor under the range of conditions which are expected to occur during the cycle and from cycle-to-cycle, may be pre-calculated in the manner described above, and programmed into the microprocessor. In those cases where it is acceptable to assume that parameters, such as ambient temperature, ambient relative humidity, ambient pressure, pump air flow rate, chamber temperature, and weight percentage of hydrogen peroxide vapor, will remain constant, the values for such parameters can also be pre-programmed into the microprocessor.

In addition, where ambient temperature, ambient relative humidity, ambient pressure, pump air-flow rate, chamber temperature, and weight percentage of hydrogen peroxide vapor can be presumed to remain constant, the above-described calculations for determining the rate of sterilant injection, in response to chamber pressure, can be reduced to the following, where K is a constant:

$$IR\ (\text{mg/min}) = C\ \text{sat} \times \%\ \text{sat} \times K \times P$$

The foregoing equation can be used to carry out a particularly economical and efficient embodiment of the invention, where it is acceptable to maintain the percentage of saturation limit within a range of percentages, preferably between about 85 to about 95%. In this embodiment, the rate of sterilant injection is adjusted to a series of pre-set rates, to reach an instantaneous saturation limit percentage within the predetermined percentage range, in response to a corresponding series of continuous and adjacent, predetermined pressure ranges. Prior to sterilant injection, the chamber pressure is sensed, and the rate of sterilant flow is then adjusted to the pre-set injection rate corresponding to the pressure range that includes the measured chamber pressure.

To illustrate an example of the foregoing embodiment of the invention, a series of injection rates and a corresponding series of pressure ranges were established for maintaining the percentage of instantaneous saturation limit (for hydrogen peroxide vapor generated from 31% by weight hydrogen peroxide solution) within about 85% to about 95%, under flow-through conditions, using the exemplary endoscope sterilization illustrated in FIG. 1 (to be described in further detail later herein).

To begin, a series of injection rates was experimentally determined by delivering the hydrogen peroxide solution through an injection valve pulsing at on/off valve times ranging from 10–17 msec (msec of time per 4 seconds total on/off time), at constant pressure of about 150 mm Hg). The observed injection rates and corresponding on/off valve times are reported in Table I.

Then, a series of endoscopes, representative of those intended for use in the sterilization system of FIG. 1, were placed in the system and subjected to flow-through sterilization at ambient pressure (about 760 atm) and ambient temperature (about 25° C.), a chamber temperature of 38° C., and a pump air flow rate of about 10 liters/min. Relative humidity remained below a maximum of 90%. The chamber pressure was observed to range from about 120 mm Hg to about 220 mm Hg (depending on the nature of the endoscope). Based on this observation, it was determined that the series of pressure ranges corresponding to the previously determined injection rates would extend from a minimum of 120 mm Hg to a maximum of 220 mm Hg.

Next, iterations of calculations were carried out using the equations previously described, to match the predetermined injection rates with ranges of chamber pressures that would provide an instantaneous saturation limit percentage (for the hydrogen peroxide vapor generated from the 31% by weight hydrogen peroxide solution) between about 85–95%. In carry out these calculations, ambient temperature and pressure were assumed to remain constant at 25° C. and 760 atm, respectively, the chamber temperature was assumed to remain constant at 38° C., pump air flow was assumed to remain constant at 10 liters/min., and ambient relative humidity was assumed, for the purpose of the example, to remain constant at 90%. The selected chamber pressure ranges and their corresponding injection rates, resulting from the foregoing calculations, are listed in Table I. Calculated instantaneous hydrogen peroxide vapor concentrations and saturations limit percentages, for each injection rate and the minimum/maximum pressures of its corresponding pressure range, are also provided in Table I.

TABLE I

| On/Off Time, msec | Injection Rate, mg/min | Chamber Pressure mm Hg (psia) | [Vaporized $H_2O_2$] mg/l | % Sat. |
|---|---|---|---|---|
| 17 | 735 | 120 (2.32) | 3.43 | 84 |
|  |  | 132 (2.55) | 3.80 | 94 |
| 16 | 690 | 133 (2.56) | 3.59 | 89 |
|  |  | 141 (2.73) | 3.80 | 95 |
| 14 | 657 | 142 (2.74) | 3.64 | 91 |
|  |  | 147 (2.84) | 3.78 | 95 |
| 13 | 630 | 148 (2.85) | 3.66 | 92 |
|  |  | 154 (2.98) | 3.79 | 96 |
| 12 | 570 | 155 (2.99) | 3.43 | 87 |
|  |  | 166 (3.21) | 3.71 | 95 |
| 12 | 519 | 167 (3.22) | 3.39 | 87 |
|  |  | 182 (3.52) | 3.69 | 96 |
| 11 | 465 | 183 (3.53) | 3.34 | 87 |
|  |  | 200 (3.87) | 3.62 | 96 |
| 10 | 411 | 201 (3.88) | 3.24 | 86 |
|  |  | 220 (4.25) | 3.55 | 96 |

As indicated in Table I, under the given conditions, the series of injection rates (e.g., 735, 690, 657 mg/min, etc.) corresponds to a series of chamber pressure ranges, ranging from 120 mm Hg to 220 mm Hg (e.g., 120 to 132 mm Hg, 133–141 mm Hg, 142–147 mm Hg, etc.). Each injection rate setting, when selected in response to a chamber pressure falling within its corresponding pressure range, will yield a saturation limit percentage ranging between about 85 % to about 95%. For example, if the measured chamber pressure ranges between 120 to 132 mm Hg, the injection rate can be set at 735 mg/min, and the resulting saturation limit percentage will fall within the desired range of about 85 to about 95%. As another example, if the measured chamber pressure ranges between 155 to 166 mm Hg, the injection rate can be set at 570 mg/min, and the resulting saturation limit percentage will again remain between about 85 to about 95%.

A relatively inexpensive injection valve, for metering and controlling the flow of sterilant liquid to the vaporizer, can be used in carrying out the above-described embodiment of the present invention. The injection valve only needs a single setting for each range of chamber pressures, i.e., each chamber pressure does not require its own injection rate setting. Any suitable known injection valve, capable of consistently delivering the series of pre-set injection rates, can be employed.

When the above-described embodiment of the invention is carried out with a microprocessor, under the given conditions (such as ambient temperature which are assumed to remain constant) the series of pre-set injection rates and corresponding series of continuous pressure ranges can be programmed into the microprocessor. Since it has already been determined that the selected injection rates will provide the desired saturation limits and percentages, under the given conditions, there is no need to input additional (sensed or calculated) data, such as the saturation limits, ambient relative humidity, air flow rates, etc., which are otherwise used to calculate the adjusted injection rate in the manner previously described herein. The microprocessor may merely receive an input signal representative of the chamber pressure, prior to injection, and automatically adjust the injection rate to the pre-set rate corresponding to the pressure range which includes the measured pressure. It is also contemplated that pre-determined series of injection rates and corresponding pressure ranges can be determined for different sets of conditions (such as ambient temperature, ambient relative humidity, etc.), and stored together in the microprocessor, for use in regulating sterilant injection rates under a wider range of conditions.

For example, in an alternative embodiment of the present invention, a humidity sensor is employed to measure the actual humidity of the air flow entering the system. Expanded data tables are created, through iterations of the previously described calculations, in which the range of relative humidities expected to be encountered are substituted for 90% relative humidity. The expanded data tables are then used to control the injection rate, based upon the measured humidity, as well as measured chamber pressure, further optimizing the efficacy of sterilization.

The method of the present invention will now be further described with reference to the sterilization cycle illustrated in FIG. 2 and the endoscope sterilization system illustrated in FIG. 1. As previously stated, in the illustrated example, the rate of sterilant injection is adjusted, in response to chamber pressures measured prior to injection, pursuant to the present invention, from points F to H of the sterilization cycle enlarged in FIG. 3.

The sterilization system includes a source of liquid sterilant 10, which in the illustrated example is aqueous hydrogen peroxide, and a liquid level sensor 66 for the liquid sterilant source 10. The system also includes a set of vacuum pumps 12, a vaporizer 14, three-way valve 16, air injection valve 18, air inlet valve 20, by-pass valve 22, suction valve 24, and a sterilization chamber, which in the illustrated example is a sealable and removable cassette 26. The cassette is described in commonly assigned, copending application U.S. Ser. No. 07/851,096, entitled "Device and System for Sterilizing Objects," now abandoned in favor of copending continuation application Ser. No. 08/282,228, filed on Jul. 29, 1994, and incorporated by reference herein.

The cassette 26 includes an inlet port 28 for receiving the flow of vapor sterilant and carrier gas, which in the illustrated example is room air, and an outlet port 30 for exhausting gases from the cassette 26. The outlet port 30 (or inlet port 28) of the cassette is fluidly coupled with one end of an endoscope (not depicted) or other lumened instrument, via a manifold connector 32. Sterilant vapor bathes the external surfaces of the endoscope and passes through the lumens, when sterilant vapor is injected and withdrawn from the cassette 26, through ports 28 and 30. Thus, the endoscope or other instrument may be contacted with sterilant vapor and sterilized both inside and outside.

A suitable known temperature sensor 40, such as a thermocouple or a resistive temperature device is positioned in the exhaust gas line near outlet port 30, to monitor the internal temperature of the cassette.

A first suitable known pressure sensor 42, such as a pressure transducer or digital pressure meter, is positioned in the inlet gas line near inlet port 28, to monitor the internal cassette pressure. A second suitable pressure sensor 44, which may be used to check for leaks in the system, is positioned in the exhaust line near the outlet port 30. The second pressure sensor 44 and temperature sensor 40 may be conveniently housed together with a biological indicator 58 for monitoring sterilization efficacy, as illustrated, or may be housed separately.

A suitable known humidity sensor 60 is positioned in the inlet gas line downstream of HEPA air filter 50, to monitor the relative humidity of the room air entering the system.

A suction valve 24 is positioned in the exhaust line between outlet port 30 and pumps 72. The outlet ends of pumps 12 are fluidly connected to a converter 46 for reducing hydrogen peroxide vapors to water vapor and oxygen, thereby removing vapor phase hydrogen peroxide from the exhausted gases.

Pumps 12, which are preferably two-stage oil-free vacuum pumps, create a downstream negative pressure differential and draw aqueous hydrogen peroxide from its source 10 through a particulate filter 48 to the three-way mixer valve 16. Three-way valve 16, when opened through path A-C is continuously pulsed (alternately with air injection valve 38 and valve 16, opened through path B-C) so that discrete increments of liquid approximating a steady stream pass through path A-C of valve 16 to the vaporizer 14. Pursuant to the method of the present invention, three-way valve 16 regulates the rate of flow of liquid sterilant from its source 10, to the vaporizer, where vaporized sterilant is injected into the flow of carrier gas, in response to the chamber pressure sensed by pressure sensor 42, prior to injection.

Room air is drawn through an HEPA air filter 50, through the air injection valve 18 through path B-C of valve 16 to the vaporizer 14, and/or through air inlet valve 20 into the vaporizer 14. A flow restrictor 52 is provided in-line, upstream of the vaporizer inlet, causing room air to pass also through the flow restrictor 52 to the vaporizer 14, when air inlet valve 20 is opened (unless by-pass valve 22 is opened to divert most of the air path through it). The flow restrictor 52 serves to maintain vacuum conditions during the transition and flow-through phases.

The vaporizer includes a temperature sensor 54, as well as a vaporizer heater 56. A surface of the vaporizer is heated and maintained at a predetermined temperature sufficient to vaporize liquid phase sterilant on contact with the heated surface.

At the start of the cycle shown in FIG. 2, the endoscope is connected to the cassette 26, and the cassette 26 is sealed and fluidly coupled at its inlet port 28 and outlet port 30, to the input and exhaust lines of the sterilization system, respectively. The cassette 26 is then placed in a warming cabinet 34, which includes a suitable known temperature sensor 64 for monitoring the internal temperature of the cabinet 34, a blower 36 and heater 38.

During an optional warming phase (points A to B), the vaporizer 14 is pre-heated by heater 56. Air drawn by blower 36 over heater 38 circulates through and pre-heats the warming cabinet 34. The cassette 26 or its contents are pre-heated by allowing air to flow unrestricted (through opened by-pass valve 22 and air inlet valve 20) through the heated vaporizer to the cassette 26. The cassette 26 may also be pre-heated through convection by warm air circulating in the warming cabinet 34.

Following the warming phase, three-way valve 16, air injection valve 18, air inlet valve 20, and by-pass valve 22 are closed, suction valve 24 is opened, and the cassette 26 is pulled down (points B to C of FIG. 2) to a pressure of about 30 mm Hg absolute. Port A-C of valve 16 is then opened and sterilant is drawn from source 10 through port A-C of valve 16 to the vaporizer 14, alternatively with air drawn through opened port B-C of three-way valve 16 and opened air injection valve 18, in amounts sufficient to produce a slight positive pressure upstream of the vaporizer 14. The vapor pressure of the sterilant carries it to inlet 28 (due to the presence of the vacuum and the slight positive air pressure) where it is introduced to the cassette 26 (points C to D of FIG. 2). The deep vacuum injections raise the chamber pressure about 10–13 mm Hg. The pressure rise is monitored by pressure sensor 44. There is a brief deep vacuum hold period (where three-way valve 16, air injection valve 18 and suction valve 24 are closed, points D to E of FIG. 2), lasting about 15 seconds.

Then, at the beginning of the transition phase (point E), suction valve 24 is opened and air laden with sterilant vapor is injected into the cassette 26 in nearly continuous pulses (10 msec bursts of hydrogen peroxide vapor every 4 seconds) through three-way valve 16 and air injection valve 18. The chamber pressure rapidly rises (points E to F) to about 120 mm Hg. As the injection pulses continue (points F to G), the chamber pressure rises to between 120–220 mm Hg. During this latter portion of the transition phase (points F to G), when the chamber pressure is less rapidly increasing, the rate of each injection is adjusted, in response to the chamber pressure sensed by pressure sensor 42 prior to injection, to obtain a hydrogen peroxide vapor concentration that is between about 85% to about 95% of the instantaneous saturation limit existing immediately after the hydrogen peroxide and carrier gas are introduced into the cassette 26.

Figure 3:
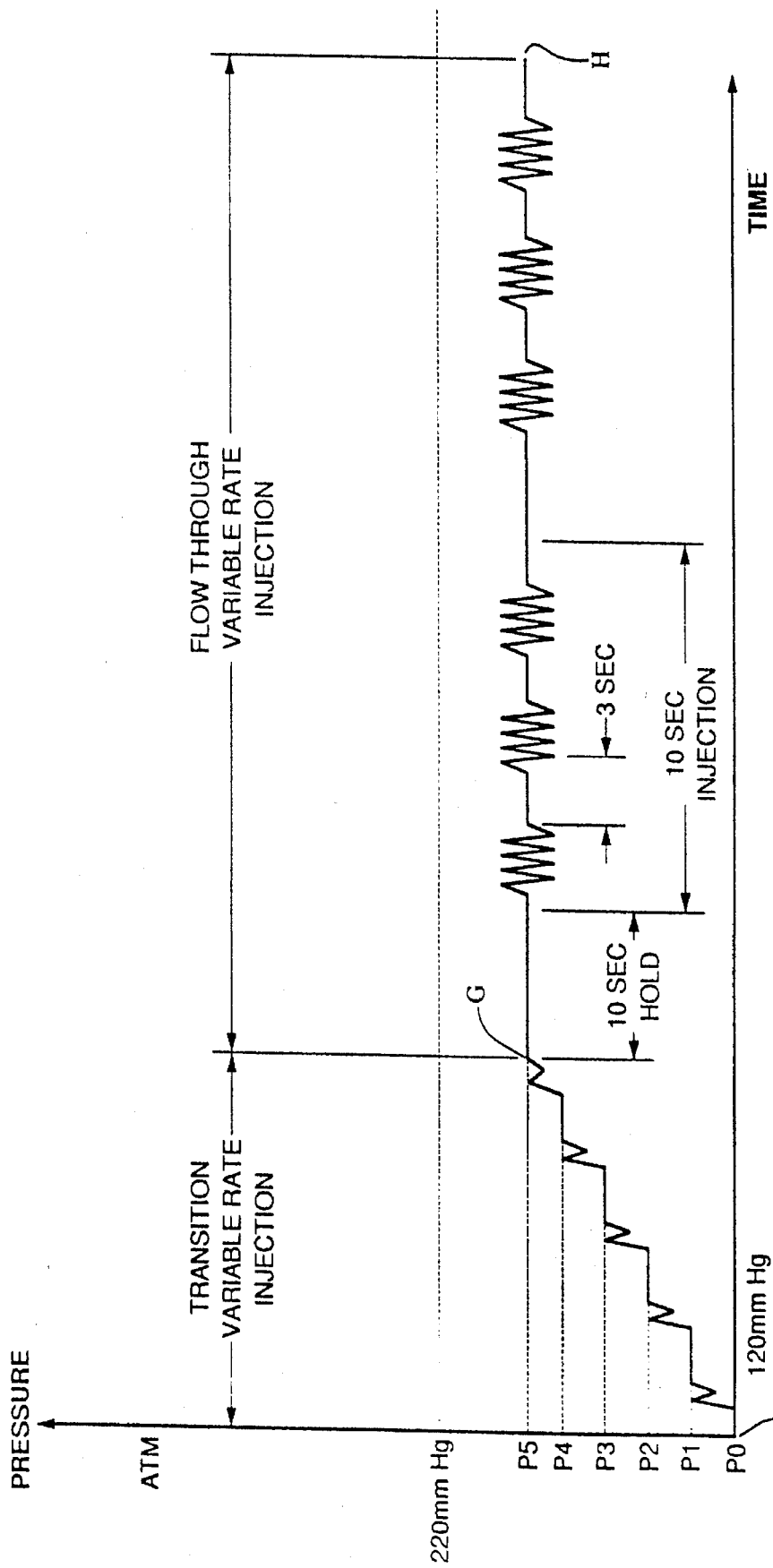
FIG. 3 is an enlarged portion of the graph of FIG. 2.

During the flow-through phase (points G to H of FIG. 2) there are successive alternating 10 second sterilant injection periods and 10 second static holding periods, where the injections are discontinued. The suction valve 24 is closed during the static holding periods and opened during the injection periods. Injection valve 18 and path B-C of three-way valve 16 pulse continuously and alternatively with path A-C of three-way valve 16, whenever suction valve 24 is open, but are never continuously open. As indicated in FIG. 3, during the injection periods, the pulses of sterilant vapor are spaced three seconds apart.

During the flow through phase (points G to H), the rate of each injection is again adjusted in response to the chamber pressure sensed by pressure sensor 42, prior to injection, to obtain a hydrogen peroxide vapor concentration between about 85% to about 95% of the saturation limit existing immediately after the hydrogen peroxide and carrier gas into the cassette 26.

By regulating the rate of sterilant injection during the flow-through phase and a portion of the transition phase, in response to chamber pressure, pursuant to the method of the present invention, the efficacy of sterilization is optimized, and condensation of hydrogen peroxide is avoided.

Figure 5:
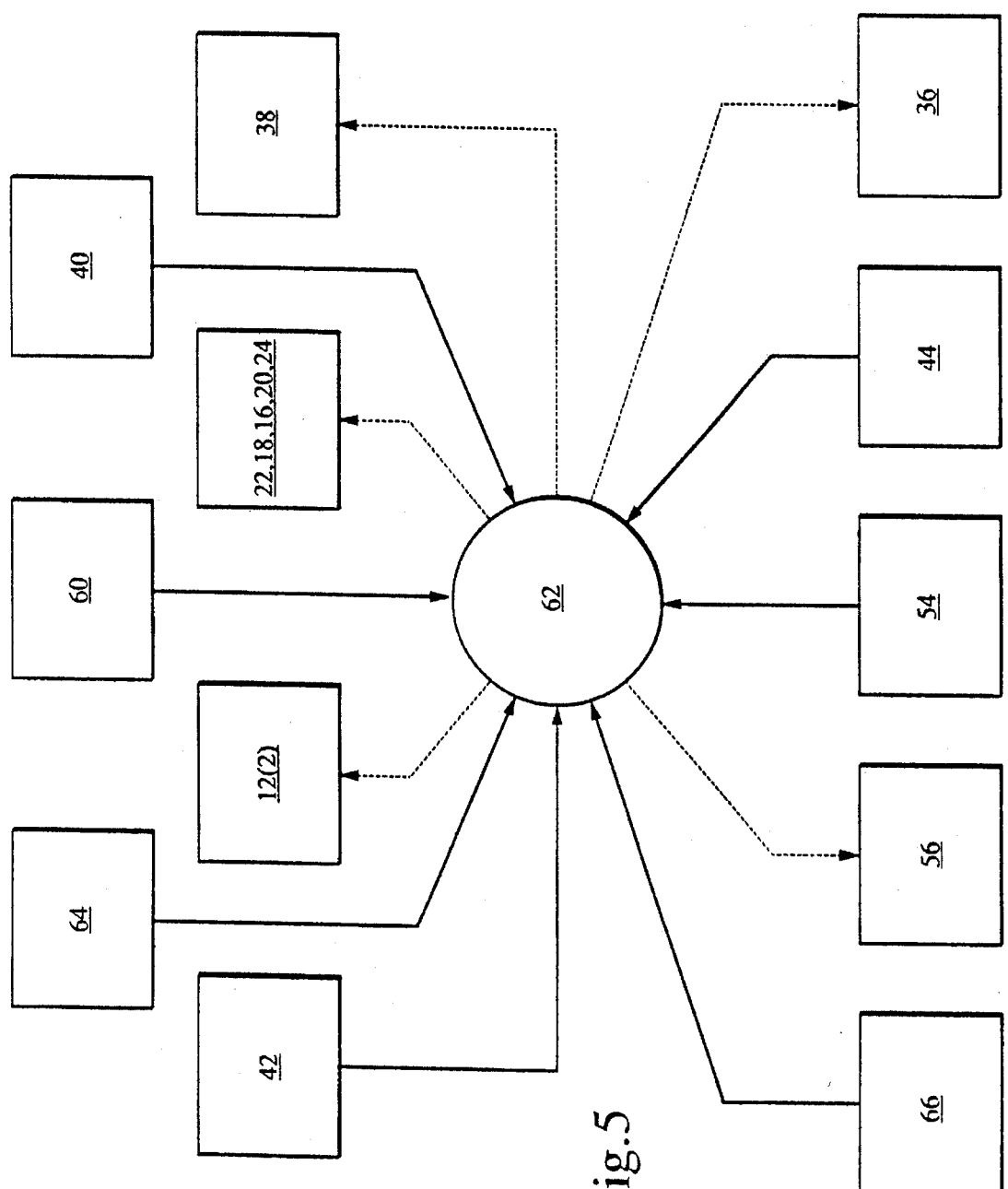
FIG. 5 is a schematic diagram illustrating the interfaces between a microprocessor and other components of a computerized version of the sterilization system depicted in FIG. 1.

In FIG. 5, a schematic diagram of a computerized version of the sterilization system depicted in FIG. 1 is provided. A microprocessor 62 interfaces with the various components of the sterilization system, as illustrated in FIG. 5. The microprocessor 62 receives input signals (represented by the solid lines in FIG. 5) from the pressure sensors 42 and 44, humidity sensor 60, temperature sensors 40, 54, and 64, and liquid level sensor 66. In response to these input signals, the microprocessor is programmed to control through output signals (represented by the dotted lines in FIG. 5) the operations of valves 18, 22, 16, 20 and 24, the pumps 12, the cabinet heater 38 and blower 36, and vaporizer heater 56.

Figure 4:
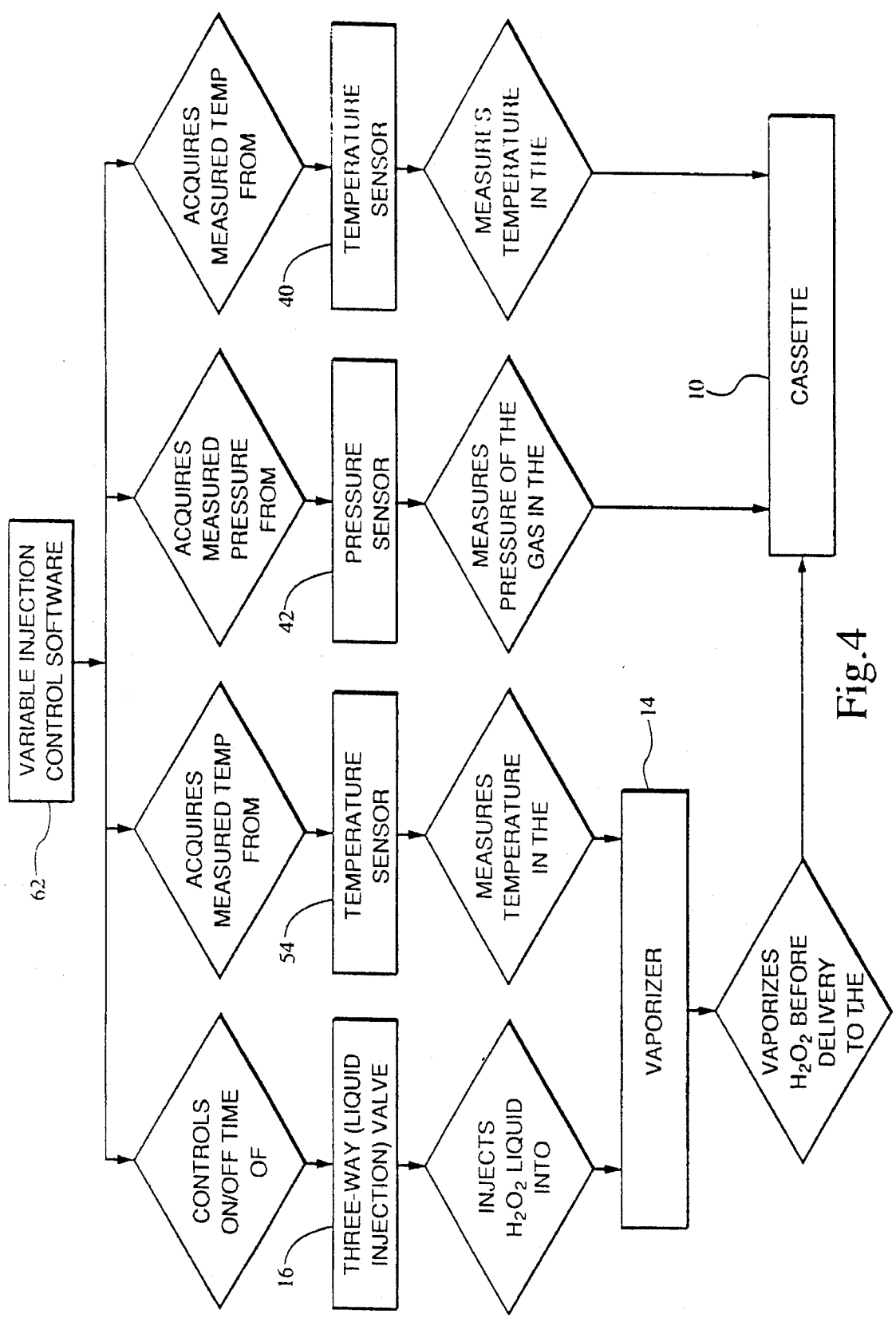
FIG. 4 is an information diagram illustrating the operations carried out in a computerized version of the invention, by components of the exemplary system illustrated in FIG. 1.

Turning to FIG. 4, an information diagram illustrating the operations carried out by a computerized version of the sterilization system depicted in FIG. 1 is provided. In the illustrated example, the microprocessor 62 has been programmed to regulate the rate of delivery of liquid sterilant through three-way valve 16 to vaporizer 14, during the second portion of the transition phase and flow-through phase of the sterilization cycle represented in FIG. 2, by controlling the on/off time of three-way valve 16 in response to measured chamber temperatures and pressures so that the instantaneous saturation limit percentage of hydrogen peroxide vapor delivered to the cassette 10 is between 85–95%. In particular, the microprocessor 62 has been pre-programmed with a series of sterilant injection rates and corresponding series of pressure ranges, which have been previously determined for the ranges of chamber temperatures and pressures which are expected to be encountered during operation of the sterilization system. In FIG. 4, ambient pressure, ambient temperature, ambient relative humidity, concentration of hydrogen peroxide solution, and pump air flow are assumed to remain constant.

The microprocessor 62 receives an input signal from temperature sensor 54 which is representative of the temperature in the vaporizer. When the vaporizer has reached the desired vaporization temperature level, the sterilization cycle begins. Prior to the variable rate injections made during the sterilization cycle, the microprocessor 62 receives an input signal from pressure sensor 42 which is representative of the pressure in the cassette 10, and an input signal from temperature sensor 40 which is representative of the temperature measured in the cassette 10.

In response to the measured chamber pressure and temperature, the microprocessor 62 sets the on/off time of three-way valve 16 to provide a rate of delivery of hydrogen peroxide to the vaporizer 14 and cassette 10, such that the instantaneous saturation limit percentage falls between 85–95%.

While the invention has been described herein with reference to the preferred embodiments, it is to be understood that it is not intended to limit the invention to the specific forms disclosed. On the contrary, it is intended to cover all modifications and alternative forms falling within the spirit and scope of the invention.

What is claimed is:

1. A system for optimizing sterilization with a sterilant vapor, comprising:

a sterilization chamber comprising an inlet port and an outlet port, said chamber being fluidly connected to a vacuum means;

an injection assembly for injecting a sterilant vapor into a carrier gas;

means for flowing the sterilant vapor and carrier gas into the chamber through the inlet port, through the chamber, and out of the chamber through the outlet port;

a measuring unit for predetermining the relative humidity, pressure and temperature of the carrier gas;

a sensing unit for sensing a characteristic in the sterilization chamber during a sterilization cycle, said characteristic selected from the group consisting of pressure and temperature;

a first regulating unit for regulating the rate of injection of the sterilant vapor into the carrier gas to maintain a predetermined percentage of the instantaneous saturation limit for the sterilant vapor in the chamber, wherein the rate of sterilant vapor injection is responsive to the sensed characteristic in the chamber and the predetermined relative humidity, pressure and temperature of the carrier gas.

2. The system according to claim 1, further comprising:

means for predetermining a range of chamber pressures which correspond to a predetermined range of percentages of the saturation limit for the sterilant vapor in the chamber;

a second regulating unit for regulating the rate of sterilant vapor injection into the carrier gas to reach and maintain the predetermined range of percentages of the saturation limit for the sterilant vapor in the chamber immediately following introduction of the sterilant vapor and carrier gas into the chamber, wherein the rate of sterilant vapor injection is responsive to the corresponding, predetermined range of pressures which includes the sensed pressure in the chamber.

3. The system according to claim 1, wherein the sterilization chamber is a cassette.

4. The system according to claim 3, further comprising an item to be sterilized having at least two open ends and a fluid path there-between and a connector to couple said item at one end to the inlet port or outlet port of the sterilization chamber.

* * * * *